(12) United States Patent
Riether et al.

(10) Patent No.: US 9,791,468 B2
(45) Date of Patent: **\*Oct. 17, 2017**

(54) TRANSPORT DEVICE, SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Christian Riether, Muehltal (DE); Achim Sinz, Waiblingen (DE)

(73) Assignee: Roche Diagnostics Operations, Inc., Indianapolis, IN (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/665,411

(22) Filed: Mar. 23, 2015

(65) Prior Publication Data

US 2015/0276777 A1  Oct. 1, 2015

(30) Foreign Application Priority Data

Mar. 31, 2014  (EP) .................................... 14162950

(51) Int. Cl.

| | | |
|---|---|---|
| *G01N 35/10* | (2006.01) | |
| *G01K 13/12* | (2006.01) | |
| *G01N 35/04* | (2006.01) | |
| *G01N 35/00* | (2006.01) | |

(52) U.S. Cl.
CPC ............ *G01N 35/10* (2013.01); *G01K 13/12* (2013.01); *G01N 35/04* (2013.01); *G01N 2035/00445* (2013.01); *G01N 2035/0477* (2013.01)

(58) Field of Classification Search
CPC ..................................................... G01N 35/10
See application file for complete search history.

(56) References Cited

U.S. PATENT DOCUMENTS

| | | |
|---|---|---|
| 3,273,727 A | 9/1966 | Rogers et al. |
| 2,653,485 A | 4/1972 | Donlon |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A \* | 6/1992 | Saito ........................ B01L 1/02 34/625 |
| 5,295,570 A | 3/1994 | Grecksch et al. |
| 5,309,049 A | 5/1994 | Kawada et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Sean E Conley
*Assistant Examiner* — Matthew Krcha
(74) *Attorney, Agent, or Firm* — Roche Diagnostics Operations, Inc.

(57) ABSTRACT

A transport device for receiving a sample container and for transporting the sample container on a transport surface, the transport device being capable of being moved magnetically over the transport surface and, further, having a cooling device is presented. A sample distribution system comprising such a transport device and to a laboratory automation system is also presented.

13 Claims, 2 Drawing Sheets

(56) References Cited

U.S. PATENT DOCUMENTS

| | | |
|---|---|---|
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Talmayr |
| 6,141,602 A | 10/2000 | Igarashi et al. |
| 6,151,535 A | 11/2000 | Ehlers |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,428,957 B2 | 9/2008 | Schaefer |
| 7,578,383 B2 | 8/2009 | Itoh |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether et al. |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1* | 1/2009 | LaBarre ............ B01L 3/5027 435/303.1 |
| 2009/0022625 A1 | 1/2009 | Lee et al. |
| 2009/0081771 A1* | 3/2009 | Breidford ......... B01L 3/5027 435/305.1 |
| 2009/0128139 A1 | 5/2009 | Drenth et al. |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1* | 6/2010 | Dai .................. G01N 35/10 700/245 |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1* | 12/2012 | Shah .................. G01N 1/312 700/103 |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276778 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |

FOREIGN PATENT DOCUMENTS

| | | |
|---|---|---|
| DE | 3909786 A1 | 9/1990 |
| DE | 102012000665 | 8/2012 |
| DE | 102011090044 A1 | 7/2013 |
| EP | 0601213 A1 | 6/1994 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |

(56) References Cited

FOREIGN PATENT DOCUMENTS

| | | | |
|---|---|---|---|
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1966 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 3-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 4/1994 |
| JP | 06-148198 A | 5/1994 |
| JP | 6-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/085670 A1 | 7/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

\* cited by examiner

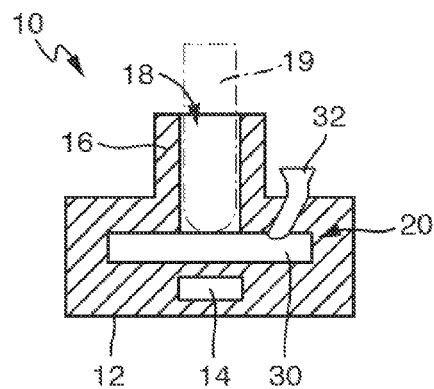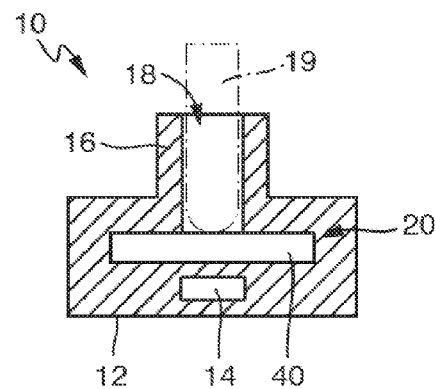
Fig. 1  Fig. 2
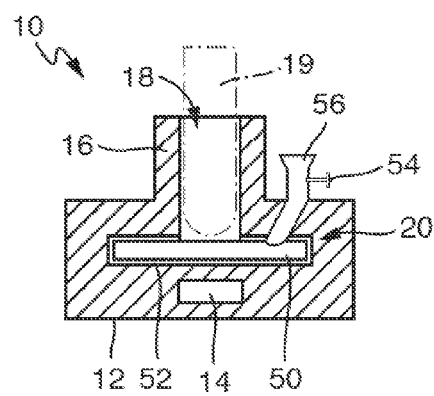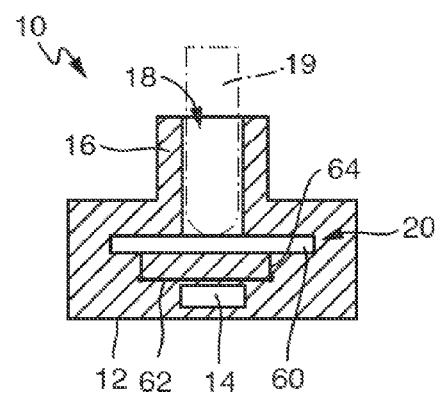
Fig. 3  Fig. 4

TRANSPORT DEVICE, SAMPLE DISTRIBUTION SYSTEM AND LABORATORY AUTOMATION SYSTEM

CROSS-REFERENCE TO RELATED APPLICATIONS

This application claims priority to EP 14162950.1 filed Mar. 31, 2014, which is hereby incorporated by reference.

BACKGROUND

The present disclosure generally relates to a transport device for receiving a sample container and for transporting the received sample container between pre-analytic, analytic and/or post-analytic stations of a laboratory automation system, to a sample distribution system and to a laboratory automation system.

There is a need for a transport device, a sample distribution system and a laboratory automation system which allow the flexible transport and flexible processing of samples, particularly in terms of dynamically variable waiting times until a possible treatment and/or processing of the samples in the stations.

SUMMARY

According to the present disclosure, a transport device to receive a sample container and to transport the received sample container between pre-analytic, analytic and/or post-analytic stations of a laboratory automation system is disclosed. The transport device can comprise at least one magnetically active element to interact with a magnetic field generated by at least one electromagnetic actuator such that a drive force is applied to the transport device and a cooling device to cool a sample container received by the transport device.

Accordingly, it is a feature of the embodiments of the present disclosure to provide for a transport device, a sample distribution system and a laboratory automation system which allow the flexible transport and flexible processing of samples, particularly in terms of dynamically variable waiting times until a possible treatment and/or processing of the samples in the stations. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates a transport device according to a first embodiment of the present disclosure.

FIG. 2 illustrates a transport device according to a second embodiment of the present disclosure.

FIG. 3 illustrates a transport device according to a third embodiment of the present disclosure.

FIG. 4 illustrates a transport device according to a fourth embodiment of the present disclosure.

DETAILED DESCRIPTION

Figure 5:
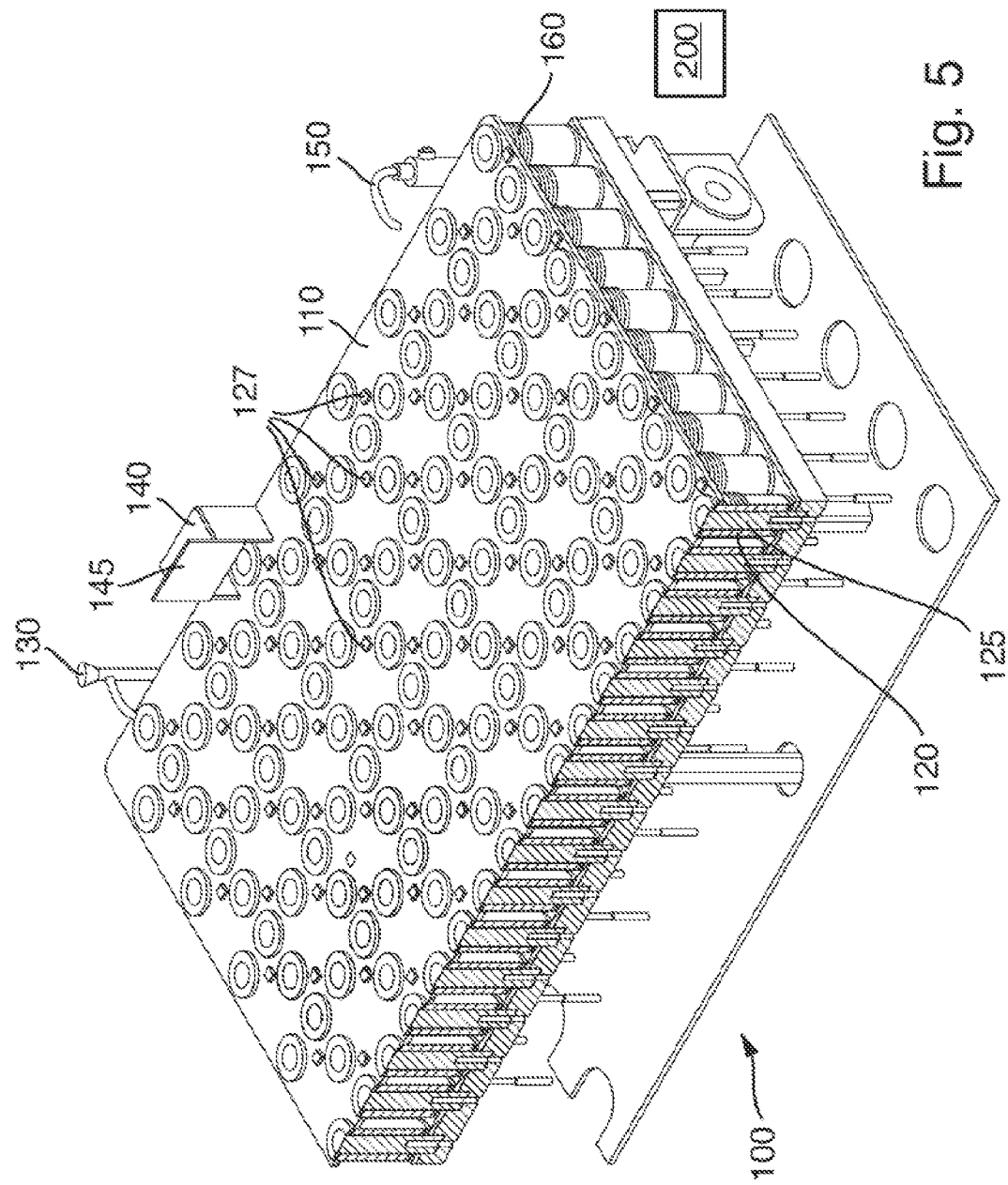
FIG. 5 illustrates a sample distribution system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A transport device for receiving at least one sample container, for example in the form of a (sample) tube, and for transporting the received sample container between pre-analytic, analytic and/or post-analytic stations of a laboratory automation system is presented. The transport device may be, for example, a sample carrier.

A pre-analytic station can serve usually for the pre-processing of samples or sample containers. An analytic station may be designed, for example, for using a sample or part of the sample and a reagent in order to generate a measurable signal, on the basis of which it can be determined whether and, if appropriate, in what concentration the analyte is present. A post-analytic station serves usually for the post-processing of samples or sample containers.

The pre-analytic, analytic and post-analytic stations may have, for example, at least one station from the set of following stations: a cap removal station for the removal of caps or seals on sample tubes, a cap application station for the application of caps or seals to sample tubes, an aliquoting station for the aliquoting of samples, a centrifuging station for the centrifuging of samples, a filing station for the filing of samples, a pipetting station for pipetting, a sorting station for the sorting of samples or sample tubes, a sample-tube type determination station for determining a type of a sample tube, and a sample-quality determination station for determining sample quality.

The transport device can comprise at least one magnetically active element, for example in the form of one or more permanent magnets and/or in the form of ferromagnetic material. The magnetic element can interact with a magnetic field generated by at least one electromagnetic actuator, in such a way as to apply a drive force to the transport device or to the magnetically active element. The transport device can further comprise a cooling device for cooling a sample container received or held in the transport device.

By the transport device, it can be possible to leave samples on the transport surface for a longer time than compared to a conventional transport device not comprising a cooling device. By the use of the cooling device, the temperature of the sample can be lowered, so that most chemical processes can be slowed down. This can delay undesirable chemical modifications in the sample which may distort the analysis result.

In a typical transport device, a single cooling device may be present. However, a plurality of cooling devices, for example two or three cooling devices, for example of a different type, may also be provided in a respective transport device.

According to one embodiment, the cooling device can have a container for receiving a substance. This can be a chemical substance. In may be a pure substance or a mixture of different substances. Such a substance may be designed to absorb heat during a reaction. This can enable the sample to be cooled by the chemical reaction of the substance which can extract heat from the sample.

The substance may perform phase transition between the solid and the liquid phase at a temperature of between about −20° C. and about 0° C. Such phase transition can usually require an especially large amount of energy which can be extracted from the surroundings, that is to say, mainly from the sample. This can allow especially efficient cooling of the sample.

Such a substance can be, for example, salt water or a gel. Substances of this kind can have suitable phase transition temperatures and require a large amount of heat for such phase transition.

According to one embodiment, the cooling device can have a latent-heat store. This can typically be a body which can be arranged in the transport device and which can perform phase transition at a specific temperature. For such phase transition, energy may be required, which can be extracted from the surroundings. This energy can be extracted essentially from the sample, thus allowing especially efficient cooling.

According to one embodiment, the cooling device can have a container for receiving a cryogenic liquid. Such a container can typically be designed to be especially well insulated from the surroundings, so that as small a fraction of the cryogenic liquid as possible evaporates on account of heat delivered from outside. Instead, the introduction of heat to the cryogenic liquid is as far as possible to take place solely from the sample. Especially good cooling of the sample can consequently be achieved. For example, a container for receiving a cryogenic liquid can have a jacket which is evacuated. Undesirable heat conduction can consequently be prevented especially well.

The container for receiving a cryogenic liquid may be designed for receiving liquid nitrogen. It may also be designed for receiving liquid helium. Nitrogen has a relatively high boiling point, as compared with helium, but can be markedly more cost-effective and simpler to handle than liquid helium. By contrast, liquid helium can afford the advantage of an especially low boiling point.

The container for receiving a cryogenic liquid can be filled with a cryogenic liquid, such as, for example, liquid nitrogen or liquid helium. The desired cooling action can consequently be achieved.

According to one embodiment, the cooling device can have a Peltier element and an associated energy supply unit. The energy supply unit can be designed for supplying the Peltier element with operating energy. By use of a Peltier element, gentle and efficient cooling of the sample can be achieved. Moreover, the space requirement of Peltier elements can typically be relatively small. Moreover, the embodiment with a Peltier element can offer the advantage that cooling can basically be maintained for an unlimited time, in so far as electrical energy is continually delivered by the energy supply unit.

According to one embodiment, the cooling device can have a heat pump and an associated energy supply unit. The use of a heat pump may have, in particular, advantages in terms of efficiency, as compared with the use of a Peltier element.

An energy supply unit may preferably have an energy absorption unit which can be designed for absorbing energy wirelessly. This may be, for example, an induction coil. The energy can, in this case, be typically emitted by an energy transmission unit which can be arranged outside the transport device. For example, the energy transmission unit may be arranged underneath a transport surface. It may be formed, for example, by an arrangement comprising a plurality of coils or by one sufficiently large coil, with the result that a magnetic alternating field can be generated.

The transport device may comprise a temperature sensor. The temperature sensor can measure a temperature of the received sample container and/or measure a temperature of a sample contained in the received sample container. The temperature sensor may, for example, measure a surface temperature of the received sample container at a specific position of the sample container, e.g. at the bottom of the sample container. The temperature sensor may be in direct contact with the sample container. The transport device may active its cooling device only if the measured temperature exceeds a given threshold. The transport device may implement a thermostat.

The transport device may comprise data transmitter. The data transmitter can wirelessly transmit the measured temperature e.g. to a control device of a sample distribution system. The data transmitter may, for example, be Bluetooth data transmitter, RFID (radio-frequency identification) data transmitter, near-field data transmitter and the like. For that purpose, the transport device may comprise an energy storage for providing the energy needed for data transmission. Alternatively, the data transmitter (and the temperature sensor) may be incorporated as a passive RFID-Tag.

The transport device may have thermal insulator for thermally insulating a sample container received in the transport device from its surroundings. The required cooling capacity can consequently be reduced, because an introduction of heat into the sample can be reduced by the insulator. This can also reduce the energy quantity which has to be extracted from the sample again in order to maintain a specific temperature lying below room temperature. Furthermore, what can be achieved by the insulator can be that a greater heat flow from the sample to the cooling device can take place, whereas the heat flow from the surroundings to the cooling device can be suppressed.

A sample distribution system is also disclosed. The sample distribution system can comprise a plurality of transport devices, for example, a few tens to a few hundreds of transport devices or sample carriers. The sample distribution system can further comprise a transport surface designed for carrying the transport devices.

The sample distribution system can further comprise a plurality of electromagnetic actuators arranged stationarily under the transport surface. The electromagnetic actuators can move a transport device arranged on the transport surface by the exertion of a magnetic force upon the transport device.

The sample distribution system can further comprise a control device for activating the electromagnetic actuations in such a way that a transport device on the transport surface can move along a predeterminable, such as, a two-dimensional movement path. The transport surface may be a planar surface, beneath which the electromagnetic actuators can be arranged. The magnetically active element may be a permanent magnet and/or ferromagnetic material. This can make it possible to have a simple and reliable design.

A plurality of transport devices can be understood to mean one transport device or a plurality of transport devices. In principle, any number of transport devices may be an integral part of the sample distribution system.

The electromagnetic actuators may be designed as electromagnets which can be activated and their polarity reversed simply and accurately, so that they can generate a defined magnetic field. Consequently, in interaction with the magnetically active element of a respective transport device, the transport device can be moved.

The control device may an electronic control device. This may be, for example, a computer, a microprocessor or a programmable logic controller. The control device may have a processor and storage. The storage may store program code, upon the implementation of which the processor can behave in a defined way.

According to one embodiment, the sample distribution system can have a cooling chamber for the reception of transport devices for cooling transport devices and/or their cooling devices which can be contained therein. This can make it possible to reactivate a cooling device, contained in a transport device, in the cooling chamber, for example when its cooling capacity is exhausted. The corresponding transport device can subsequently be used again for reception, transportation and cooling of samples.

The cooling chamber may comprise a device for the cooling of air in the cooling chamber, while a temperature which lies about 5 K to 10 K below ambient temperature can prevail in the cooling chamber. For example, the device for the cooling of air may a conventional air-conditioning installation. By a transport device having a corresponding cooling device, for example with a latent-heat store, being introduced into the cooling chamber, the cooling device can be cooled and consequently reach its cooling capacity for the cooling of samples.

According to one embodiment, the sample distribution system can have an energy transmission unit for the wireless transmission of energy to a transport device. This may be an arrangement of induction coils. Such an embodiment can be advantageous when a corresponding coil is located in the transport device which can be an energy absorption unit. It can thus be possible to transmit energy to a transport device, wherein this energy can be utilized to operate in the transport device a cooling device which requires electrical energy to be operated, that is to say, for example, a Peltier element.

According to one embodiment, the sample distribution system comprises a device for pouring a cryogenic liquid and/or chemicals into a respective vessel of a respective transport device. This can be advantageous especially when a corresponding vessel or corresponding container for receiving a cryogenic liquid or a chemical or substance is located in at least one transport device which can be used in the sample distribution system. The cooling capacity of such a transport device can consequently be restored.

The sample distribution system may comprise data receiver. The data receiver can wirelessly receive measured temperatures from the respective transport devices located on the transport surface. The data receiver can correspond to the respective the data transmitter of the transport devices.

The laboratory automation system can comprise a plurality (for example, between two and twenty) of pre-analytic and/or analytic and/or post-analytic stations for treating or processing sample containers and/or samples contained in the sample containers. Treatment or processing may comprise, for example, reading of a barcode, removal of a cap on the tube, centrifuging of the sample, aliquoting of the sample, analyzing the sample, etc. The laboratory automation system can further comprise a sample distribution system for transporting or distributing the sample containers between the pre-analytic, analytic and post-analytic stations.

The control device of the sample distribution system may be determine a waiting time until a sample container and/or a sample contained in the sample container can be treated by a station. The waiting time may be an expected, planned and/or theoretical waiting time. The waiting time can be determined essentially by a waiting time of the corresponding sample container and/or of the sample contained therein until treatment/processing in the pre-analytic, analytic and post-analytic station. The waiting time may be calculated or determined, for example, using specific formulae and/or tables. In the simplest instance, the waiting time can be determined from the length of a waiting queue in front of a station.

The sample distribution system or the laboratory automation system may comprise a device for activating the cooling device of a transport device. The device may be actuated when the waiting time of the transport device exceeds a threshold value. This can make it possible to leave samples normally, without special cooling, on the sample distribution system and distribute them to corresponding analysis stations, in so far as their expected waiting time is not yet critical. Only when a sample has remained too long on the sample distribution system is the corresponding cooling device activated. Energy can consequently be saved. The device for activating the cooling device may additionally or alternatively be actuated by the control device if the received measured temperature exceeds a threshold value.

For example, the device for activating the cooling device can activate an energy supply in order to activate a cooling device, based on a Peltier element, in a transport device. The device for activating the cooling device may, for example, also move a transport device into a cooling chamber, and in this case, cool the cooling device and thus activate it. The device for activating the cooling device may, for example, also cause a cryogenic liquid, such as, for example, liquid nitrogen or liquid helium or a suitable chemical substance, to be poured into the cooling device of the transport device. All this can serve to provide a defined cooling capacity for the sample, so that the latter can remain on the transport surface of the sample distribution system for a longer time without any chemical modification.

The sample distribution system and/or the laboratory automation system may comprise a central temperature measuring device. The central temperature measuring device may measure respective temperatures of sample containers and/or of samples contained in the sample containers being arranged on the transport surface. The cooling device of a transport device may be activated, if the measured temperature exceeds a threshold value, thus implementing a thermostat. The central temperature measuring device may e.g. be embodied as an infrared thermometer or as an infrared camera.

FIGS. 1 to 4 show respective transport devices 10 according to first to fourth exemplary embodiments, in each case in sectional side view. The transport devices 10 are constructed essentially identically, in particular externally.

The transport devices 10 can have in each case an underside 12, by which the transport device 10 can lie on a transport surface of a sample distribution system and slide over this transport surface. Above the underside 12 can be arranged a permanent magnet 14 which can make it possible, by the provision of an external magnetic field, to exert a force upon the transport device 10. The transport device 10 can consequently be moved over the transport surface by a suitable activation of electromagnets of a sample distribution system.

On the top side, the transport devices 10 can have in each case an insulating ring 16, in which a sample receptacle 18 can be formed centrally. The sample receptacle 18 can, in this case, be designed as a recess in the insulating ring 16, so that a sample container in the form of a sample tube 19 can be plugged into the sample receptacle 18 and be held there. The insulating ring 16 can prevent the lateral introduction of heat into the sample tube 19 and into a mostly liquid sample located therein.

The respective transport device 10 can further comprise a cooling device 20. The transport devices 10 according to the first to fourth exemplary embodiments can differ from one another in their cooling device 20, as is explained in more detail below.

The sample receptacle 18 can terminate directly above the cooling device 20 of the transport device 10, so that, in the event that the cooling device 20 performs a cooling function, heat can be drawn out of the sample tube 19 contained in the sample receptacle 18 and out of a sample located therein.

In the transport device 10 according to the first exemplary embodiment illustrated in FIG. 1, the cooling device 20 can have a vessel or container 30 for receiving a chemical substance. The container 30 can be connected to a filler connection piece 32, via which a chemical substance can be introduced into the containers 30. Such a substance may be, for example, a gel having a plurality of chemicals which, upon reaction with one another, can absorb heat. This can be therefore an endothermic reaction. For example, a mixture of sodium bicarbonate and tartaric acid or citric acid in water can be used for this purpose. After the end of the reaction, refilling of the container 30 can usually be indicated, in order to restore the cooling capacity.

In the transport device 10 according to the second exemplary embodiment illustrated in FIG. 2, the cooling device 20 can have a latent-heat store 40 which can perform phase transition which can absorb energy. In contrast to most chemical reactions, such as may be used in a transport device 10 according to the first exemplary embodiment, this can be a reversible phase transition. This can make it possible, by cooling the transport device 10 according to the second exemplary embodiment, for example in a cooling chamber, to cancel the the endothermic face transition and consequently restore the cooling capacity of the latent-heat store 40. For example, saline water may be used for the latent-heat store 40.

In the transport device 10 according to the third exemplary embodiment illustrated in FIG. 3, the cooling device 20 can have a container 50 for reception of cryogenic liquids. The container 50 can comprise, in this case, insulation 52 in the form of an evacuated space. The insulation can ensure that an introduction of heat into a cryogenic liquid contained in the container 50 can take place as far as possible only from a sample tube 19 contained in the sample receptacle 18.

To fill the container 50 with a cryogenic liquid, a filler connection piece 56 can be provided. In order to prevent the cryogenic liquid 50 from running out after filling and, moreover, prevent an undesirable introduction of heat into the cryogenic liquid from outside, furthermore, a slide 54 can be provided so that the filler connection piece 56 can be closed.

In the transport device 10 according to the fourth exemplary embodiment illustrated in FIG. 4, the cooling device 20 can have a Peltier element 60 and an energy supply device in the form of a coil 62. The Peltier element 60 and the coil 62 can be connected to electrical leads 64. This can make it possible, by the application of an external magnetic alternating field, to induce in the coil 62 a current which can be transmitted via leads 64 to the Peltier element 60. The Peltier element 60 can consequently perform a cooling function for the sample receptacle 18 and thus can cool a sample tube received therein and having a sample contained therein. It should be understood that a rectifier circuit may also be required for this purpose.

FIG. 5 shows a sample distribution system 100. The sample distribution system 100 can comprise a transport surface 110, on which transport devices, for example a transport device 10 according to one of FIGS. 1 to 4, can be placed and on which these can slide. For the sake of simplification, FIG. 5 does not illustrate a transport device 10, and in this respect reference may be made to FIGS. 1 to 4.

The sample distribution system 100 can be an integral part of a laboratory automation system having a number of pre-analytic, analytic and post-analytic stations, not illustrated in any more detail, which are arranged adjacently to the transport surface 15. The sample distribution system 10 can serve for transporting the sample containers between these stations.

Underneath the transport surface 110, a number of coil-shaped electromagnets 120 having respective ferromagnetic cores 125 can be provided. By use of these electromagnets 120, which can be activated individually, transport devices 10 can be moved over the transport surface 110 by their respective permanent magnets 14. Further, to determine a respective position of a transport device 10, sensors 127 can be provided on the transport surface 110.

The electromagnets 120 and the sensors 127 can be connected to a control device 200 which can have a processor and storage, not illustrated in any more detail, and which can move the transport devices 10 over the transport surface 110 by the electromagnets 120. The sample distribution system 100 can further comprise a device for cooling devices 20 in respective transport devices 10 can be activated.

The sample distribution system 100 can have a filler connection piece 130 which can dispense a mixture of chemical substances for filling a vessel or container 30 into a filler connection piece 32. Consequently, the cooling device 20 of a transport device 10 according to the first exemplary embodiment can be filled and thereby activated.

The sample distribution system 100 can further comprise a cooling chamber 140 which can be closed by an automatically actuable sliding door 145. When a transport device 10 according to the second exemplary embodiment is moved into the cooling chamber 140, the endothermic phase transition of the latent-heat store 40 can be cancelled so that the latent-heat store 40 can be suitable again for cooling.

The sample distribution system 100 can further comprise a filling station 150 for cryogenic liquids, which can be designed for introducing liquid nitrogen into a vessel 50 of a transport device 10 according to the third exemplary embodiment. The cooling device 20 of a transport device 10 according to the third exemplary embodiment can consequently be activated.

Furthermore, underneath the transport surface 110, a layer of induction coils 160 which can generate a magnetic alternating field above the transport surface 110 can be formed. These can be designed as additional windings around the electromagnets 120. A cooling device 20 of a transport device 10 according to the fourth exemplary embodiment can consequently be supplied with electrical energy, so that a sample can be cooled by the Peltier element 60.

The control device 200 can determine, for a sample in a sample carrier 10, how long the sample can be expected to stay on the transport surface 110. In so far as this value is too high to enable a largely unchanged quality of the sample to be ensured, the control device can activate the cooling device 20 of the transport device 10 by one of the measures described above. For a transport device 10 according to the first exemplary embodiment, the control device 200, for example, can move the transport device 10 to the filler connection piece 130 and can introduce a chemical to the vessel 30. For a transport device 10 according to the second exemplary embodiment, the control device 200 for example, can move the transport device 10 into the cooling chamber 140 and consequently activate the latent-heat store 40. If the transport device 10 is a transport device according to the third exemplary embodiment, the control device can move this to the filling station 150 and can introduce liquid nitrogen into the vessel 50 in order thereby to activate the cooling device 20. If the transport device 10 is a transport device according to the fourth exemplary embodiment, by the induction coils 160, the control device 200 can generate an electromagnetic alternating field above the transport surface 110, so that the Peltier element 60 can cool the sample. A longer duration of stay of the sample on the transport surface 110 can consequently be managed in an advantageous way, without chemical changes in the sample being caused.

It should be understood that a sample distribution system 100 may also have only one of the methods (130, 140, 150, 160) shown for activating a cooling device or a choice of two or three of the methods (130, 140, 150, 160) shown. This can be advantageously to be coordinated with the type of transport devices used.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

The invention claimed is:

1. A laboratory automation system, the laboratory automation system comprising:
   a plurality of pre-analytic, analytic and/or post-analytic stations to process sample containers and/or samples being contained in the sample containers; and
   a sample distribution system to distribute the sample containers between the pre-analytic, analytic and/or post-analytic stations, the sample distribution system comprising,
   a plurality of transport devices, wherein each transport device is configured to receive a sample container and to transport the received sample container between the pre-analytic, analytic and/or post-analytic stations, each transport device comprising,
   at least one magnetically active element to interact with a magnetic field generated by at least one electromagnetic actuator, and
   a cooling device configured to cool a sample container received by the transport device,
   a transport surface configured to carry the plurality of transport devices,
   a plurality of electromagnetic actuators arranged under the transport surface, wherein the electromagnetic actuators are configured to move a transport device arranged on the transport surface by applying a magnetic force to the transport device; and
   a control device configured to activate the electromagnetic actuators such that a transport device moves along a predeterminable movement path on the transport surface, wherein the control device of the sample distribution system is configured to determine a waiting time until a respective sample container and/or a sample contained in the respective sample container can be treated by a station, wherein the cooling device is configured to cool the sample container if the waiting time exceeds a threshold value.

2. The laboratory automation system according to claim 1, wherein the cooling device comprises a container for receiving a substance.

3. The laboratory automation system according to claim 2, wherein the substance, upon reaction, is configured to absorb heat and cool the sample container.

4. The laboratory automation system according to claim 1, wherein the cooling device has a latent-heat store.

5. The laboratory automation system according to claim 1, wherein the cooling device has a container for receiving a cryogenic liquid.

6. The laboratory automation system according to claim 1, wherein the cooling device has a Peltier element and an associated energy supply unit.

7. The laboratory automation system according to claim 6, wherein the energy supply unit has an energy absorption unit which is designed to absorb energy transmitted wirelessly.

8. The laboratory automation system according to claim 1, further comprises, a temperature sensor to measure a temperature of the received sample container and/or measure a temperature of a sample contained in the received sample container.

9. The laboratory automation system according to claim 8, further comprises, a data transmitter to wirelessly transmit the measured temperature to a control device of a sample distribution system.

10. The laboratory automation system according to claim 1, further comprises, a cooling chamber to receive transport devices and to cool the received transport devices and/or the cooling devices contained in the received transport devices.

11. The laboratory automation system according to claim 1, further comprises, an energy transmission unit to transmit energy to a transport device wirelessly.

12. The laboratory automation system according to claim 1, further comprises a data transmitter to wirelessly receive measured temperatures from the transport devices.

13. The laboratory automation system according to claim 1, wherein the cooling device of a transport device is configured to cool the sample container if the received measured temperature exceeds a threshold value.

* * * * *